United States Patent [19]

Caugant et al.

[11] Patent Number: 4,559,641
[45] Date of Patent: Dec. 17, 1985

[54] RETRACTABLE CASSETTE HOLDER FOR A RADIOLOGICAL AND RADIOGRAPHIC EXAMINATION APPARATUS

[75] Inventors: Jean Caugant, Chevilly Larue; Guy Stephan, Maison Alfort, both of France

[73] Assignee: Thomson-CGR, Paris, France

[21] Appl. No.: 621,076

[22] Filed: Jun. 15, 1984

[30] Foreign Application Priority Data

Jun. 24, 1983 [FR] France ................ 83 10502

[51] Int. Cl.$^4$ .......................... G11B 1/00; G03B 41/16
[52] U.S. Cl. .................................. 378/181; 378/189; 378/205; 378/209; 378/176
[58] Field of Search ............... 378/176, 181, 189, 205, 378/209

[56] References Cited

U.S. PATENT DOCUMENTS

| | | | |
|---|---|---|---|
| 3,222,518 | 12/1965 | Nagel | 378/189 |
| 3,976,887 | 8/1976 | Holzermer et al. | 378/181 |
| 4,232,227 | 11/1980 | Finkenzeller et al. | 378/181 |
| 4,333,014 | 6/1982 | Renshaw | 378/181 |
| 4,432,095 | 2/1984 | Adelmeyer et al. | 378/176 |

FOREIGN PATENT DOCUMENTS

| | | |
|---|---|---|
| 2744139 | 4/1979 | Fed. Rep. of Germany . |
| 3036932 | 12/1981 | Fed. Rep. of Germany . |
| 3022248 | 5/1982 | Fed. Rep. of Germany . |
| 2161229 | 6/1973 | France . |
| 2267078 | 4/1975 | France . |

Primary Examiner—Richard L. Schilling
Attorney, Agent, or Firm—Roland Plottel

[57] ABSTRACT

The invention provides a retractable cassette holder for a combined X ray and radiographic examination apparatus. This cassette holder forms a mobile assembly comprising means for forming a recess with variable dimensions in the middle thereof and means for causing the barrel of a luminance amplifier to slide within this recess.

9 Claims, 5 Drawing Figures

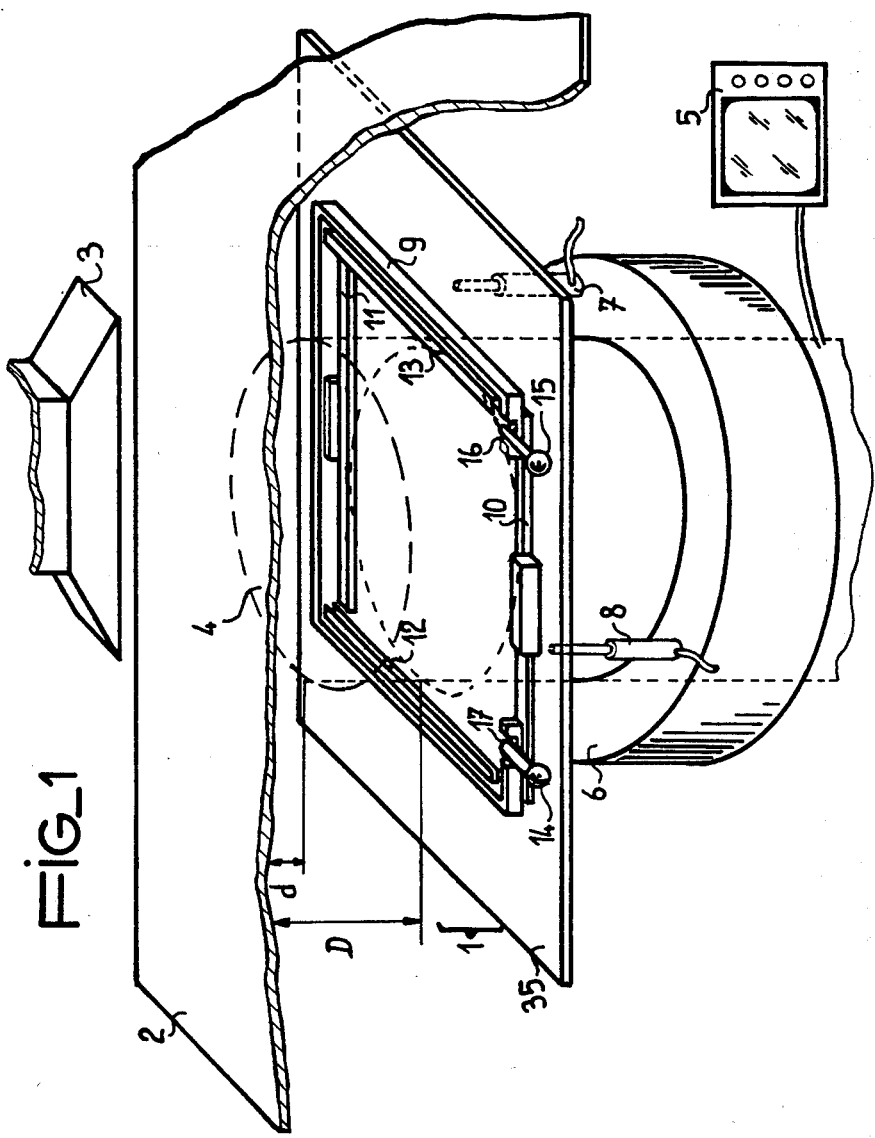

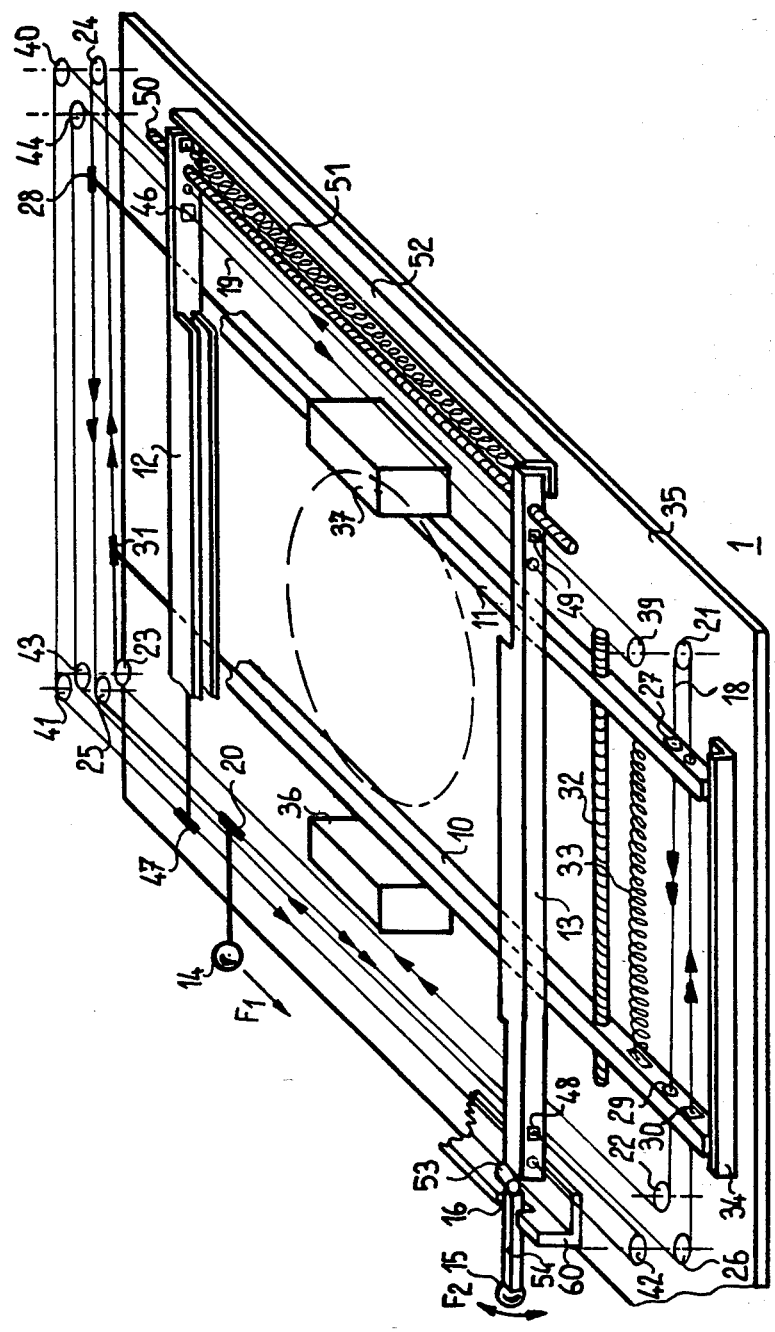

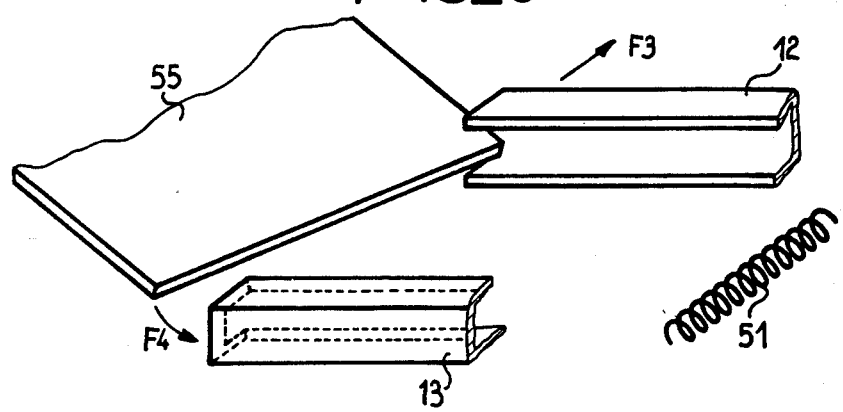
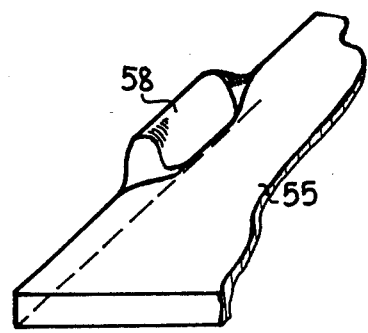
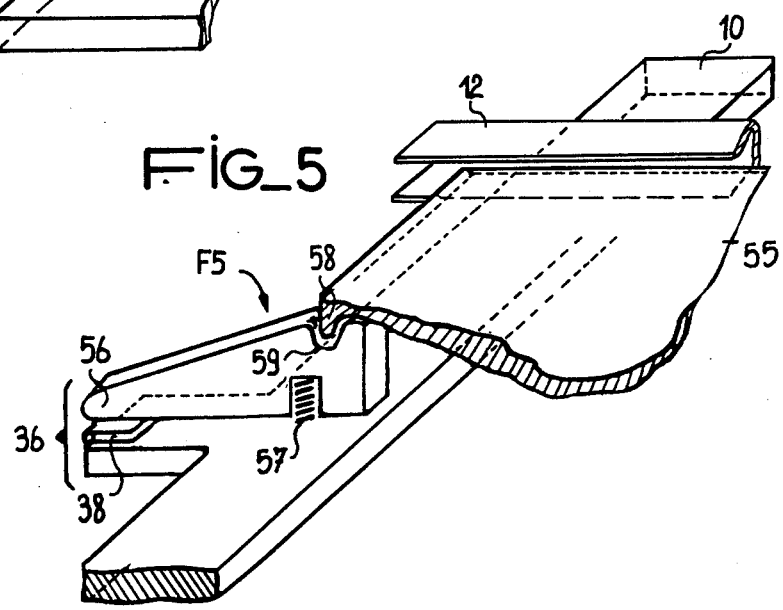

RETRACTABLE CASSETTE HOLDER FOR A RADIOLOGICAL AND RADIOGRAPHIC EXAMINATION APPARATUS

BACKGROUND OF THE INVENTION

The invention relates to a retractable cassette holder for a radiological and radiographic examination apparatus. It applies more especially to the medical field where such apparatus are widely used.

FIELD OF THE INVENTION

An apparatus for radiological examination comprises essentially a radioactive source and a radiation detector situated in the radioscopic field of this source. A patient to be examined is laid on a patient carrying table so as to be positioned between the radioactive source and the detector in the path of the radiation. The detector is connected to a display device which gives a radiological image of a zone of a patient irradiated by the radioactive source. An apparatus for radiographic examination also comprises a radioactive source, a patient carrying table and instead of the detector, a radio sensitive film for giving a radiographic image of the irradiated zone of the patient.

For reasons of safety in handling, the radio sensitive films are contained in cassettes which are in general standardized and adapted to the dimensions of the films. A cassette containing a radio sensitive film is placed in the radioscopic field of the source before irradiation by means of a cassette holder. To obtain better definition of the radiographic image, the cassettes and so the cassette holder are disposed as close as possible to the patient carrying table. It is known to fasten the cassette holder to the table itself. So as to allow a radiographic image to be taken of any one part of the body of the patient, the cassette holder is fastened to the table by means of slides formed in this table and providing, for any part of the patient, optimum positioning of the cassette.

A radioactive radiation detector comprises a luminance amplifier. The purpose of luminance amplifiers is essentially to amplify the irradiating radiation, after it has passed through the patient, by transforming it into a more intense radioelectric radiation and from which detection is then carried out in general by means of a video camera. For reasons identical to that in radiography, the luminance amplifier of the radiological chain must be placed as close as possible to the patient carrying table.

This proximity requirement prevents, in both cases, the cassette holder and the luminance amplifier from being permanently located together directly above or below the radioactive source for allowing the successive use, and alternately in each of the two modes, of the combined radiological and radiographic examination apparatus. This solution is all the less practical since the cassette holder comprises a metal base, for holding the cassette over the whole of its surface and since this metal base forms an obstacle for the radiation to be measured in the case of radiological use. To overcome this disadvantage, it is known, during radiological use, to move the cassette holder along the table so that it leaves the radioscopic field of the source. For radiographic use, the luminance amplifier is moved away so as to allow positioning of the cassette holder.

DESCRIPTION OF THE PRIOR ART

In current use, such a combined examination apparatus operates alternatively as a radiological device for locating the zones of the body of the patient examined and as a radiographic device for taking a radiographic image of the located zone. Besides the problems of centering the cassette holder on the radiologically studied zone, the devices of the prior art have two drawbacks. The first drawback consists in the need for iterative handling of the cassette holder and of the luminance amplifier during an examination series. The second drawback is a problem of space occupancy. In fact, when it is moved outside the radioscopic field of the source, the cassette holder forms a hindrance for the relative movement of the patient carrying table with respect to the radioactive source-luminance amplifier alignment. If we call garage position the position of the cassette holder under the patient carrying table during a radiological application, this garage position must be situated beyond the body of the patient; either beyond his feet or beyond his head. This allows a general investigation by moving the radioscopic field all along the body of the patient. This increase in space required is cumbersome. In other solutions, where a patient carrying table larger than necessary is not used, two garage positions must be defined: one towards the feet and another towards the head. Should an error occur in choosing the garage position, additional handling is required for transferring the cassette holder to the garage position where it is not troublesome. This additional handling results in wasting time and annoys the operators using the examination apparatus.

SUMMARY OF THE INVENTION

The object of the invention is to overcome the above mentioned drawbacks by proposing a cassette holder which no longer slides longitudinally with respect to the patient carrying table but may, in the garage position, slide around a barrel containing the luminance amplifier.

The invention relates to a retractable cassette holder for a radiological and radiographic examination apparatus, said apparatus comprising a patient carrying table, a radioactive source situated opposite a first face of the table for subjecting a zone of the patient to irradiation, a luminance amplifier situated opposite the second face of the table directly below the radioactive source for forming a radiological image of the irradiated zone, and a retractable cassette holder for insertion between the second face of the table and the luminance amplifier so that, when it is loaded with a radiosensitive cassette, a radiographic image of the irradiated zone may be formed, wherein said cassette holder forms a mobile assembly comprising means for forming in the middle thereof a recess having variable dimensions and means for allowing the luminance amplifier to slide inside this recess.

BRIEF DESCRIPTION OF THE DRAWINGS

The present invention will be better understood from reading the following description and referring to the accompanying figures.

This description is not limitative of the features of the invention. In these Figures, the same references designate the same parts. These Figures show:

FIG. 1: a perspective view of the cassette holder of the invention;

FIG. 2: a view of a particular construction of a cassette holder in accordance with the invention;

FIG. 3: a view of the mode of inserting a cassette into the cassette holder of the invention;

FIG. 4: a view of a cassette used;

FIG. 5: a view of a part of the cassette holder.

DESCRIPTION OF THE INVENTION

FIG. 1 shows a retractable cassette holder 1 in accordance with the invention. This cassette holder 1 is adapted for an X ray and radiographic examination apparatus comprising a patient carrying table 2, a radioactive source 3 and a cylindrical barrel 4, shown with broken lines, containing a luminance amplifier, not represented. This amplifier is connected to a display means 5, which forms an X ray image of the zone of the patient irradiated by the source 3. For the X ray use, which is shown, the other face of the luminance amplifier is placed at a distance d from the lower face of table 2. The cassette holder 1 is retractable by sliding around a barrel 4 so that its plane is located at a distance D from table 2. The distance D is greater than d. The cassette holder 1 forms then a mobile assembly carried by any transfer means, and more particularly here, by a set of three actuating cylinders disposed evenly around barrel 4 and bearing on the one hand on a frame 6 integral with the frame supporting barrel 4. Of the three actuating cylinders only two, cylinders 7 and 8, have been shown. These cylinders bear, on the other hand, under the cassette holder 1. The cassette holder 1 comprises means 9 for forming in the middle thereof a recess having variable dimensions. In the example described, in the garage position, this recess is defined by two sets of jaws, the set of jaws 10 and 11 and the set of jaws 12 and 13. This recess is thus slightly larger than the section of barrel 4 shown by a broken line curve. Each set of jaws is operable manually by means of a handle, respectively handle 14 for set 10 and 11, handle 15 for set 12 and 13. It will be noted in FIG. 1 that means 9 comprise notches respectively 17 and 16 for locking the handles 14 and 15 in a position such that the jaws 10 and 11 or 12 and 13 do not bear against barrel 4.

The operation of jaws 10 to 13 by means of handles 14 and 15 is shown in FIG. 2. These means are only one example for forming the recess. They could have any other form tending to produce the same result. They comprise the sets of jaws 10 and 11 and 12 and 13. Each of these sets of jaws is driven by an endless cable. The set of jaws 10 and 11 is driven by cable 18 shown by double arrows and the set of jaws 12 and 13 is driven by cable 19 shown by single arrows. By an action exerted on handle 14 in the direction of arrow $F_1$, tending to draw this handle 14 closer to the middle of the cassette holder 1, handle 14 firmly secured to cable 18 by the fixing means 20, drives cable 18 in the direction shown by the double arrows. Cable 18 travels along the periphery of the cassette holder so that in all positions it has two portions going in reverse directions to each other. Cable 18 is stretched between loose pulleys 21 to 26. The portion of cable 18 situated between pulley 21 and pulley 22 is firmly secured by a fixing means 27 to one end of jaw 11 whereas the portion of this cable situated between pulley 24 and pulley 25 is firmly fixed to the other end of this jaw by fixing means 28. By a judicious arrangement, when cable 18 travels over these pulleys, these two portions are driven in an identical direction causing jaw 11 to move parallel to itself.

Pulleys 21 to 26 are in the same plane. It can be seen that cable 18 passes freely through a whole 29 formed in one end of jaw 10. This jaw 10 is driven by cable 18 by means of fixing means 30 and 31 situated respectively on the portions of cable 18 contained beteen pulleys 21 and 26 and 23 and 24. Pulleys 21 to 24 are disposed at the top of a substantially square quadrilateral. Pulleys 25 and 26 are situated respectively in the extension of the diagonals 21–23 and 24–22 of this quadrilateral. Since cable 18 undergoes no elongation during its movement, it can be seen that jaw 10 moves parallel to itself in a direction opposite that of jaw 11 and, for a given movement of cable 18 that the magnitudes of movement of each of these jaws are identical.

So as to allow a perfect parallelism of the movement of jaws 10 and 11, a set of sliding bars, of which only bar 32 has been shown, ensures relative holding of jaws 10 and 11. Moreover, a return means, symbolized by a spring 33 working under extension, is fixed by its ends to each of jaws 10 and 11. It thus tends to bring jaws 10 and 11 close to one another. Jaws 10 and 11 are finally supported by a set of brackets such as 34 integral with the frame 35 of the cassette holder 1 and bearing under the ends of these jaws. The shafts of pulleys 21 and 22 are also fixed to support 35. No importance will be attached to the lever arm connecting handle 14 to the means 20 fixing it to cable 18: this is shown only to lighten the drawing. In practice, handle 14 is fixed directly to cable 18. Jaws 10 and 11 drive two stops respectively 36 and 37 which emerge from the plane formed by jaws 10 and 11.

Situated in a plane higher than a plane of jaws 10 and 11 is the plane of jaws 12 and 13. This latter plane intersects the active faces of stops 36 and 37 which will be discussed further on. Jaws 12 and 13 are driven like jaws 10 and 11, by a cable 19 travelling between pulleys 39 to 44. Pulleys 39 to 43 are loose pulleys having a common axis respectively with pulleys 21, 24, 25, 26 and 23. The loose pulley 44 is close to pulley 40 in the diagonal of pulleys 40, 42. Jaws 12 and 13 are driven, like jaws 10 and 11, by means respectively 46 and 47 and 48 and 49 fixing them to cable 19. Jaws 12 and 13 also comprise a bar 50 for maintaining their parallelism, a spring 51 for pulling them back and a set of slides such as 52 and 60 for supporting them in their movement. Jaws 12 and 13 have a useful profile in the form of a letter C for accomodating the lateral and vertical movements of a cassette. Thus, when a cassette is introduced between jaws 12 and 13, it is held in two directions by these jaws and in a third direction by the faces opposite stops 36 and 37.

Handle 15, used like handle 14 for causing a cable to move, is here fixed in the extension of jaws 13 by a hinge 53. This hinge 53 allows handle 15 to pivot in the direction of the double arrow $F_2$ so that in the garage position the stick 54 of this handle 15 is engaged in the notch 16 in slide 60. Thus, the action of the return spring 51 is neutralized and jaws 12 and 13 are held in a garage position. This arrangement has an advantage which is that of disposing handle 15 on the same side as handle 14 so as to place the assembly of these two handles 14 and 15 opposite the operator using the combined apparatus.

FIGS. 3 to 5 show the phase of introducing a cassette 55 into the cassette holder. In a first stage, the operator unlocks handle 15 and lets jaws 12 and 13 come closer together under the effect of the return spring 51. Then, grasping cassette 55, the operator introduces a corner thereof into the groove formed by jaw 12. While exerting on cassette 55 a pressure in the direction of arrow $F_3$, he simultaneously moves the two jaws 12 and 13 apart from each other. When the movement apart thereof is sufficient, he straightens up (arrow $F_4$) the cassette 55 for introducing it directly into jaws 12 and 13.

Stop 36 (FIG. 5) is retractable. In a particular embodiment, it has the general shape of a dihedron and is pivotably mounted at its top 56 by a hinge 38 to jaw 10. It may be retracted in the direction of arrow $F_5$ in the opposite direction to return spring 57 acting under compression. This return spring 57 bears on the one hand on stop 36 and on the other on jaw 10. Cassettes 55 (FIG. 4) generally comprise a protuberance 58 situated on their lower part, cassette 55 of FIG. 4 is shown upside down. Protuberance 58 is engaged, during positioning of the cassette, in a notch 59 formed in the upper plane of the dihedron of stop 36. Once this result has been reached, the operator unlocks handle 14 held in notch 17 and he operates this handle so as to move jaw 10 in the direction of jaw 11 so that the front end of cassette 55 comes into abutment against the active face of stop 37. The means for fixing the jaws to their respective cables are adjusted experimentally so that these jaws are permanently at an equal distance from the middle of the recess formed. Thus, whatever the dimension of the cassette, even it is not standardized, centering on the radiographed zone is obtained automatically.

In a completely automatic version, the jaws may be driven by motors actuatable by control buttons. Finally, activation of the sliding means 7 and 8 may be provided at the same time as the activation of the means tending to move barrel 4 away from the patient carrying table. However, considering the small amount of space taken up in the height direction by the cassette holder of the invention, in particular because it no longer comprises a metal base, moving barrel 4 further away becomes optional.

What is claimed is:

1. In a retractable cassette holder for a radiological and radiographic examination apparatus, said apparatus comprising a patient carrying table, a radioactive source situated opposite a first face of the table for subjecting a zone of the patient to irradiation, a luminance amplifier situated opposite the other face of the table directly below the radioactive source for forming a radiological image of the irradiated zone, and a cassette holder which is retractable so as to be insertable between the second face of the table and the luminance amplifier so as to allow, when it is loaded with a radio sensitive cassette, a radiological image to be formed of the irradiated zone, said cassette holder forms a mobile assembly comprising retracting means for moving said assembly toward and away from said table around said amplifier, means for forming a variable dimension recess in the middle thereof and means for allowing the luminance amplifier to slide inside this recess.

2. The cassette holder as claimed in claim 2, wherein the means for forming the recess comprise two sets of two facing jaws, each of the jaws of a set being able to move in a direction perpendicular to the direction of alignment of the radioactive source with the luminance amoplifier, the directions of movement of each of the two sets being substantially perpendicular to each other.

3. The cassette holder as claimed in claim 1, further comprising means so that the middle of the recess is situated in vertical alignment with the center of the luminance amplifier.

4. The cassette holder as claimed in claim 3, wherein the means for forming said recess comprise means for moving the two jaws of a set symmetrically with respect to the middle of the cassette holder.

5. The cassette holder as claimed in claim 4, wherein the means for symmetrically moving one set of jaws comprise an endless cable driving the two jaws, following a path partially surrounding the cassette holder, so that at each position of this path there exists two portions of this cable substantially parallel and travelling in reverse directions to one another.

6. The cassette holder as claimed in claim 5, wherein the means for symmetrically moving a set of jaws comprises a resilient return means tending to draw the two facing jaws closer to one another.

7. The cassette holder as claimed in claim 5, wherein the cable of a symmetrical moving means may be set in movement manually by a handle.

8. The cassette holder as claimed in claim 4, wherein the means for symmetrically moving one set of jaws comprise a self locking position, called garage position, in which the recess is at a dimension sufficient to allow the luminance amplifier to slide.

9. The cassette holder as claimed in claim 5, wherein the two sets of jaws are situated in superimposed planes.

* * * * *